United States Patent
Nielsen et al.

(10) Patent No.: US 10,976,398 B2
(45) Date of Patent: Apr. 13, 2021

(54) PROSPECTIVE RESPIRATORY TRIGGERING WITH RETROSPECTIVE VALIDATION FOR 4D-MAGNETIC RESONANCE IMAGING

(71) Applicant: KONINKLIJKE PHILIPS N.V., Eindhoven (NL)

(72) Inventors: Tim Nielsen, Eindhoven (NL); Sascha Krueger, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 602 days.

(21) Appl. No.: 15/501,031

(22) PCT Filed: Aug. 11, 2015

(86) PCT No.: PCT/EP2015/068483
§ 371 (c)(1),
(2) Date: Feb. 1, 2017

(87) PCT Pub. No.: WO2016/023910
PCT Pub. Date: Feb. 18, 2016

(65) Prior Publication Data
US 2017/0219673 A1    Aug. 3, 2017

(30) Foreign Application Priority Data
Aug. 11, 2014  (EP) .................................. 14180519

(51) Int. Cl.
*G01R 33/567* (2006.01)
*A61B 5/113* (2006.01)
(Continued)

(52) U.S. Cl.
CPC .......... *G01R 33/5673* (2013.01); *A61B 5/055* (2013.01); *A61B 5/113* (2013.01);
(Continued)

(58) Field of Classification Search
CPC ................................ A61B 5/113; A61B 5/055
See application file for complete search history.

(56) References Cited

U.S. PATENT DOCUMENTS 6,144,875 A * 11/2000 Schweikard ......... A61N 5/1049
378/69
8,526,702 B2    9/2013 Johston et al.
(Continued)

FOREIGN PATENT DOCUMENTS

| CN | 101191830 A | 6/2008 |
| CN | 103271740 A | 9/2013 |
| WO | WO2013110929 A1 | 8/2013 |

OTHER PUBLICATIONS

W0ng K.H.et al.:"Creation of 4D imaging data using open source image registration software", Pr0c. 0f SPIE, Medical Imaging 2006: Visualization, Image-Guided Procedures, and Display, vol. 6141, Feb. 12, 2006 (Feb. 12, 2006), pp. 614100-1-614100-9.
(Continued)

*Primary Examiner* — Rex R Holmes
*Assistant Examiner* — Jennifer L Ghand
(74) *Attorney, Agent, or Firm* — Sherry Austin

(57) ABSTRACT

A magnetic resonance imaging system connectable to a respiration monitor configured to provide an output signal whose level represents a respiration state. A prospective acquisition scheme for acquiring magnetic resonance images at each of a set of selected respiration states is provided, the triggering on the selected respiration states being based on predetermined threshold output signal levels of the respiration monitoring means, Respiration states at which magnetic resonance images were actually acquired, are compared with the selected respiration states according to the prospective acquisition scheme and predetermined ranges of tolerance of the selected respiration states, The prospective acquisition scheme is modified, if one of the
(Continued)

actual respiration states lies outside the predetermined range of tolerance of the selected respiration state, and magnetic resonance imaging acquisition is executed pursuant to the modified prospective acquisition scheme.

11 Claims, 4 Drawing Sheets

(51) Int. Cl.
    *G01R 33/565* (2006.01)
    *A61B 5/00* (2006.01)
    *A61B 5/055* (2006.01)

(52) U.S. Cl.
    CPC .......... *A61B 5/7207* (2013.01); *A61B 5/7221* (2013.01); *A61B 5/7292* (2013.01); *G01R 33/56509* (2013.01)

(56) References Cited

U.S. PATENT DOCUMENTS

| | | |
|---|---|---|
| 9,042,959 B2 | 5/2015 | Kassai |
| 9,599,689 B2 | 3/2017 | Horger |
| 9,651,641 B2 | 5/2017 | Praveen |
| 9,675,249 B2 | 6/2017 | Miyazaki |
| 9,713,449 B2 | 7/2017 | Goto |
| 2011/0130644 A1 | 6/2011 | Stemmer |
| 2012/0201428 A1 | 8/2012 | Joshi et al. |
| 2012/0245453 A1 | 9/2012 | Tryggestad et al. |
| 2013/0134976 A1 | 5/2013 | Sugiura |
| 2016/0349344 A1* | 12/2016 | Nielsen .............. G01R 33/4835 |

OTHER PUBLICATIONS

Y. Hu et al.: "Respiratory Amplitude Guided 4-Dimensional Magnetic Resonance Imaging", Int J Radiation Oncol Biol Phys vol. 86, No. 1, May 1, 2013 (May 1, 2013),pp. 198-204.

Baumann Tobias et al: "Temporally constrained respiratory gating improves continuously moving table MRI during free breathing.",Journal of Magnetic Resonance Imaging : JMRI Jul. 2013, vol. 38, No. 1, Jul. 2013 (Jul. 2013), pp. 198-205.

Von Siebenthal et al "4D MR Imaging of Respiratory Organ Motion and Its Variability" Phys. Med. Biol. 52, (2007) p. 1547-1564.

Tokuda et al "Adaptive 4D MR Imaging Using Navigator-Based Respiratory Signal for MRI-Guided Theraphy" Magn. Reson. Med. 59, p. 1051-1061 (2008).

* cited by examiner

US 10,976,398 B2

PROSPECTIVE RESPIRATORY TRIGGERING WITH RETROSPECTIVE VALIDATION FOR 4D-MAGNETIC RESONANCE IMAGING

CROSS REFERENCE TO RELATED APPLICATIONS

This application is a U.S. national phase application of International Application No. PCT/EP2015/068483, filed on Aug. 11, 2015, which claims the benefit of EP Application Serial No. 14180519.2 filed on Aug. 11, 2014 and is incorporated herein by reference.

FIELD OF THE INVENTION

The invention pertains to a method of operating a magnetic resonance imaging system for accurate characterization of motion of tumors and/or organs due to respiration of a subject of interest, and a magnetic resonance imaging system being operated by employing such a method.

BACKGROUND OF THE INVENTION

In the art of magnetic resonance imaging, it is known to employ four-dimensional (4D) respiratory phase-guided imaging methods for accurate characterization of motion of tumors and/or organs due to respiration of a subject of interest, usually a patient. In this regard, time is understood as the fourth dimension.

Studying motion of internal organs due to breathing is relevant for a number of medical questions. One particularly important example is the process of radiotherapy (RT) planning. The decision which technique is to be used, e.g. stereotactic radio surgery vs. conventional external beam RT, or the way how the radiation is to be applied, e.g. gated vs. continuous irradiation, is based on the amount of motion of the target tumor and the organs at risk. Using magnetic resonance imaging (MRI) to image the internal motion, as opposed to X-ray based methods, has the advantage that MRI often allows direct visualization of the structures of interest and does not rely on imaging surrogate markers as for instance implanted metal clips.

Further, T2-weighted magnetic resonance imaging is known to provide better tumor-tissue contrast than T1- or T2/T1-weighting but requires long echo times TE of about 100 ms and long pulse sequence repetition times TR in the range of about 3 s. As a consequence, these sequences are not suitable for real-time imaging. Instead, the respiratory motion is depicted by acquiring several volumetric datasets at different time-points during the respiratory cycle. These datasets are acquired by prospectively triggering the start of the acquisition with respect to the signal of a respiratory motion sensor such as a belt, a navigator or a camera.

One current method is described in the paper by Y. Hu et al., "*Respiratory Amplitude Guided 4-Dimensional Magnetic Resonance Imaging*", Int J Radiation Oncol Biol Phys, 86 (1), 198-204 (2013), wherein a method of acquiring 4D respiratory phase-guided magnetic resonance images is described which comprises a scheme of interleaving the acquisition of different points in time for different slices to be imaged in order to reduce a total acquisition time.

Using triggers at preselected respiratory levels enables acquiring MRI images at different respiratory states in different respiratory cycles and, thus, eliminates the restriction on the long pulse sequence repetition time TR. By that, more magnetic resonance imaging sequences, in particular T2-weighted magnetic resonance images, are compatible with 4D magnetic resonance imaging.

SUMMARY OF THE INVENTION

It is desirable to improve a method of operating a magnetic resonance imaging system with regard to robustness during occurrence of irregularities in a breathing pattern of a subject of interest or an output signal of a respiration monitor means.

It is therefore an object of the invention to provide an improved and robust method of operating a magnetic resonance imaging system with regard to triggering on selected respiration states of a subject of interest.

In one aspect of the present invention, the object is achieved by a method of operating a magnetic resonance imaging system, the magnetic resonance imaging system being configured for acquiring magnetic resonance images of a set of slices from at least a portion of a subject of interest over at least one breathing cycle of the subject of interest, and the magnetic resonance imaging system being connectable to a respiration monitoring means which is configured to provide an output signal whose level represents a respiration state of the subject of interest.

The method comprises:
  a step of providing a prospective acquisition scheme for acquiring within the at least one breathing cycle at least one magnetic resonance image of each slice of the set of slices at each respiration state of a set of selected respiration states of the subject of interest, the triggering on the selected respiration states being based on predetermined threshold output signal levels of the respiration monitoring means,
  a step of commencing magnetic resonance image acquisition pursuant to the provided prospective acquisition scheme, and, during executing magnetic resonance image acquisition pursuant to the prospective acquisition scheme,
  a step of comparing actual respiration states at which magnetic resonance images were actually acquired, with the selected respiration states according to the prospective acquisition scheme and predetermined ranges of tolerance of the selected respiration states,
  a step of modifying the prospective acquisition scheme, if one of the actual respiration states lies outside the predetermined range of tolerance of the selected respiration state, and
  a step of proceeding execution of magnetic resonance imaging acquisition pursuant to the modified prospective acquisition scheme.

One advantage of the method lies in that it can be ensured that the magnetic resonance images are acquired in the intended and selected respiration states, which improves an image quality of an acquired 4D magnetic resonance image data set.

Another advantage of the method lies in that it is efficient and does not significantly prolong a total elapsed time for acquiring a respiratory phase-guided magnetic resonance imaging scan package such as described by the prospective acquisition scheme.

In a preferred embodiment, the method further comprises
  a step of comparing a time course of an output signal representing a breathing cycle for which all the magnetic resonance images scheduled in the prospective acquisition scheme have been acquired, with a predetermined standard output signal time course representing a standard breathing cycle and having predetermined standard output signal ranges of tolerance, and a step of modifying the prospective acquisition scheme if the time course of the output signal representing the breathing cycle for which all the magnetic resonance images scheduled in the prospective acquisition scheme have been acquired at least partially lies outside the predetermined ranges of tolerance of the predetermined standard output signal time course.

In a suitable embodiment, an incorrect assignment of acquired magnetic resonance images to the selected respiration states can be detected and corrected for, in particular in case of the occurrence of irregularities in a breathing pattern of the subject of interest such as coughing, speaking or a higher-than-average breathing cycle, and/or in case of the occurrence of a hardware failure at the respiration monitoring means or its signal path.

Preferably, the predetermined ranges of tolerance of the selected respiration states or the predetermined standard output signal ranges of tolerance are a fixed percentage of the predetermined threshold output signal levels or the predetermined standard output signal time course, respectively. In this way, a constant relative accuracy over a total range of the selected respiration states can be achieved.

In another preferred embodiment, the step of modifying the prospective acquisition scheme comprises:
  discarding acquired data representing a magnetic resonance image corresponding to an actual respiration state that lies outside the predetermined range of tolerance of the selected respiration state, and
  adding the selected respiration state that corresponds to the actual respiration state lying outside the predetermined range of tolerance of the selected respiration state to the prospective acquisition scheme as a selected respiration state at which another magnetic resonance image is still to be acquired.

In this way, a wrong assignment of an acquired magnetic resonance image to a selected respiration state can be corrected for with high timely efficiency.

In yet another preferred embodiment, the step of modifying the prospective acquisition scheme comprises:
  discarding acquired data representing magnetic resonance images corresponding to all selected respiration states of a breathing cycle that at least partially lies outside the predetermined ranges of tolerance of the predetermined standard output signal time course, and
  adding the selected respiration states that correspond to the breathing cycle that at least partially lies outside the predetermined ranges of tolerance of the predetermined standard output signal time course to the prospective acquisition scheme as selected respiration states at which magnetic resonance images are still to be acquired.

By that, an incorrect assignment of acquired magnetic resonance images to the selected respiration states can be corrected for with a high timely efficiency, in particular in case of the occurrence of irregularities in a breathing pattern of the subject of interest such as coughing, speaking or a higher-than-average breathing cycle, and/or in case of the occurrence of a hardware failure at the respiration monitoring means or its signal path.

In another aspect of the invention, a magnetic resonance imaging system is provided that is configured for acquiring magnetic resonance images of a set of slices from at least a portion of a subject of interest over at least one breathing cycle of the subject of interest.

The magnetic resonance imaging system includes:
an examination space provided to position the subject of interest within,
  a main magnet configured for generating a static magnetic field $B_0$ in the examination space,
  a magnetic gradient coil system configured for generating gradient magnetic fields superimposed to the static magnetic field $B_0$,
  at least one radio frequency antenna device that is configured for applying a radio frequency excitation field $B_1$ to nuclei of or within the portion of the subject of interest for magnetic resonance excitation,
  at least one radio frequency antenna device that is provided for receiving magnetic resonance signals from the nuclei of or within the portion of the subject of interest that have been excited by applying the radio frequency excitation field $B_1$,
  a control unit for controlling at least one function of the magnetic resonance imaging system, and
  a signal processing unit configured for processing magnetic resonance signals to determine images of slices of at least the portion of the subject of interest from the received magnetic resonance signals.

The control unit of the magnetic resonance imaging system is configured for receiving output signals from a respiration monitoring means for triggering guidance, wherein a level of the output signal represents a respiration state of the subject of interest. The control unit is further configured to carry out steps of any embodiment of the method disclosed herein or a combination of such embodiments. With a magnetic resonance imaging system furbished in this manner, the above-mentioned objectives can advantageously be accomplished.

The respiration monitoring means may be designed as any one of commonly known types of respiration monitoring devices, such as a respiration belt type that includes a respiration sensor and is usually attached to the thorax of the subject of interest, a respiration bellows type, or one of the various known spirometer types. The respiration monitoring means may alternatively be designed as an optical camera with its lens directed to the thorax of the subject of interest. Further, the respiration monitoring means may be designed as at least one component and/or an integral function of the magnetic resonance imaging system itself, for instance a k-space navigator (FID, clover-leaf, or others) or an image navigator (1D pencil beam, 2D, 3D).

Preferably, the at least one radio frequency antenna device that is configured for applying a radio frequency excitation field $B_1$ is provided with radio frequency pulse sequences that are suitable for obtaining T2-weighted magnetic resonance images. By that, a high tumor-tissue contrast in the magnetic resonance images can be achieved.

In yet another aspect of the present invention, a software module is provided for carrying out steps of any embodiment of the disclosed method of operating a magnetic resonance imaging system with regard to triggering of magnetic resonance image acquisition, or a combination of such embodiments. The method steps to be conducted are converted into a program code of the software module, wherein the program code is implementable in a memory unit of the magnetic resonance imaging system and is executable by a processor unit of the magnetic resonance imaging system. The processor unit may be the processor unit of the control unit that is customary for controlling functions of a magnetic resonance imaging system. The processor unit may, alternatively or supplementary, be another processor unit that is especially assigned to execute at least some of the method steps.

The software module can enable a robust and reliable execution of the method and can allow for a fast modification of method steps.

BRIEF DESCRIPTION OF THE DRAWINGS

These and other aspects of the invention will be apparent from and elucidated with reference to the embodiments described hereinafter. Such embodiment does not necessarily represent the full scope of the invention, however, and reference is made therefore to the claims and herein for interpreting the scope of the invention.

In the drawings.

DETAILED DESCRIPTION OF EMBODIMENTS

Figure 1:
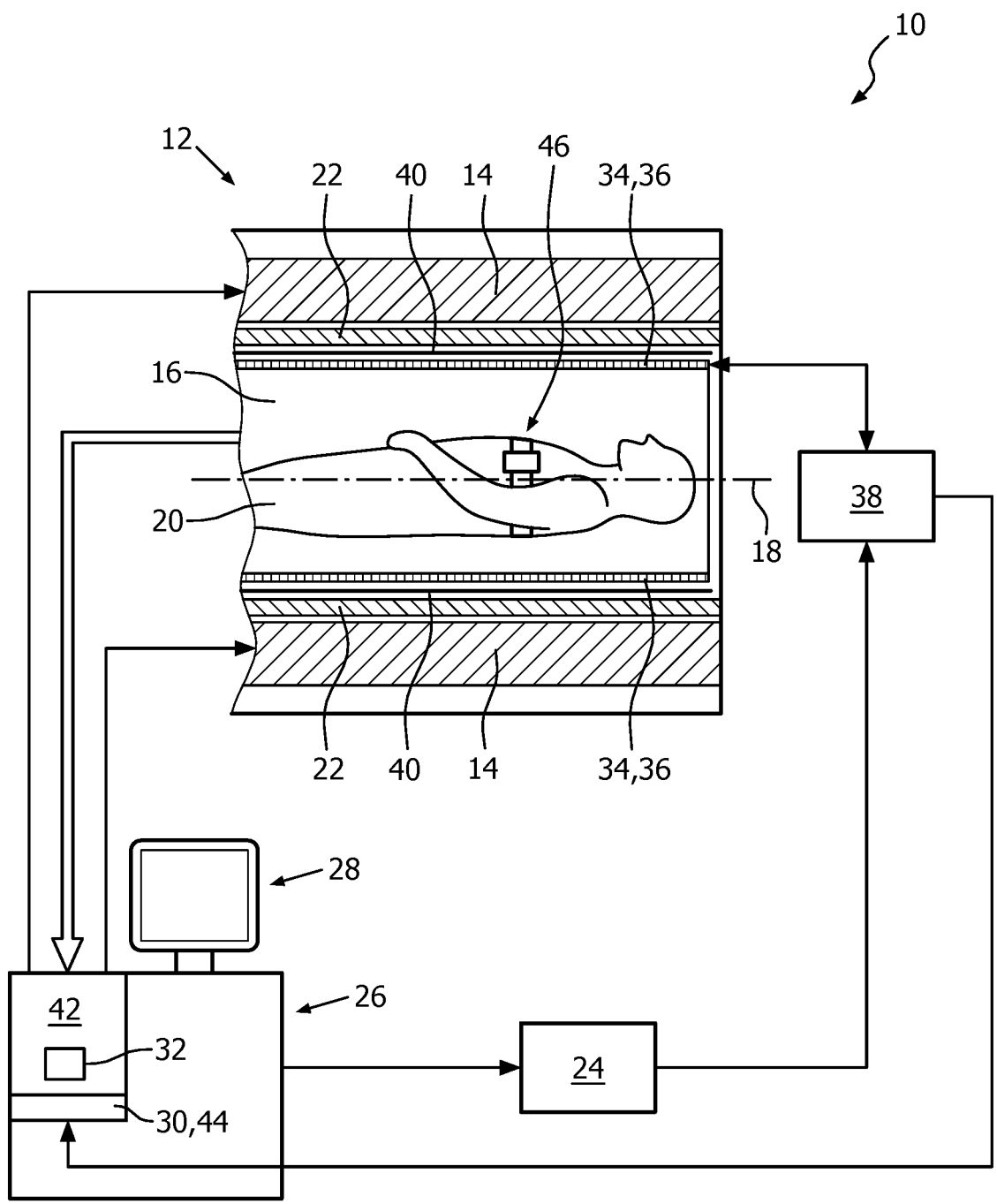
FIG. 1 shows a schematic illustration of a part of an embodiment of a magnetic resonance imaging system in accordance with the invention.

FIG. 1 shows a schematic illustration of a part of an embodiment of a magnetic resonance imaging system 10 configured for acquiring magnetic resonance images of a set of slices from at least a portion of a subject of interest 20, usually a patient, over a plurality of breathing cycles 50 of the subject of interest 20. The magnetic resonance imaging system 10 comprises a scanner unit 12 having a main magnet 14. The main magnet 14 has a central bore that provides an examination space 16 around a center axis 18 for the subject of interest 20 to be positioned within, and is further configured for generating a static magnetic field $B_0$ of 1.5 T at least in the examination space 16. For clarity reasons, a customary table top for supporting the subject of interest 20 is omitted in FIG. 1. The static magnetic field $B_0$ defines an axial direction of the examination space 16, aligned in parallel to the center axis 18. It is appreciated that the invention is also applicable to any other type of magnetic resonance imaging system providing an examination region within a static magnetic field.

Further, the magnetic resonance imaging system 10 comprises a magnetic gradient coil system 22 configured for generating gradient magnetic fields superimposed to the static magnetic field $B_0$. The magnetic gradient coil system 22 is concentrically arranged within the bore of the main magnet 14, as is known in the art.

The magnetic resonance imaging system 10 comprises a control unit 26 provided to control functions of the scanner unit 12, the magnetic gradient coil system 22, and other functions of the magnetic resonance imaging system 10. The control unit 26 includes a human interface device 28 designed as a monitor unit having a touch-sensitive screen.

Furthermore, the magnetic resonance imaging system 10 includes a radio frequency antenna device 34 designed as a whole-body coil that is configured for applying a radio frequency excitation field $B_1$ to nuclei of or within the subject of interest 20 for magnetic resonance excitation during radio frequency transmit time periods to excite the nuclei of or within the subject of interest 20 for the purpose of magnetic resonance imaging. To this end, radio frequency power is fed, controlled by the control unit 26, from a radio frequency transmitter unit 24 to the whole-body coil. The whole-body coil has a center axis and, in the operational state, is arranged concentrically within the bore of the main magnet 14 such that the center axis of the whole-body coil and the center axis 18 of the examination space 16 coincide. As is common in the art, a cylindrical metal radio frequency shield 40 is arranged concentrically between the magnetic gradient coil system 22 and the whole-body coil.

The whole-body coil is also configured as a radio frequency antenna device 36 for receiving magnetic resonance signals during radio frequency receive phases from the nuclei of or within the portion of the subject of interest 20 that have been excited by applying the radio frequency excitation field $B_1$. In an operational state of the magnetic resonance imaging system 10, radio frequency transmit phases and radio frequency receive phases are taking place in a consecutive manner.

The radio frequency transmitter unit 24 is provided to feed radio frequency power of a magnetic resonance radio frequency and in the form of turbo spin echo (TSE) radio frequency pulse sequences to the whole-body coil via a radio frequency switching unit 38 during the radio frequency transmit phases, enabling to obtain T2-weighted magnetic resonance images. During the radio frequency receive phases, the radio frequency switching unit 38, controlled by the control unit 26, directs the magnetic resonance signals from the whole-body coil to a signal processing unit 42 residing in the control unit 26. The signal processing unit 42 is configured for processing magnetic resonance signals to determine images of slices of at least the portion of the subject of interest 20 from the acquired magnetic resonance signals. Many different variations of this technique are well known to the person skilled in the art, and thus need not be described in further detail herein.

The magnetic resonance imaging system 10 further comprises a respiration monitoring means 46 that is designed as a belt-type respiration monitoring device. The respiration monitoring device includes a respiration sensor that, in an operational state, is attached to the thorax of the subject of interest 20 and is held by a belt, wound around the thorax. The respiration monitoring device is configured to provide the control unit 26 with an output signal 48 (FIG. 2) whose level represents a respiration state of the subject of interest 20. To this end, an output line (not shown) of the respiration monitoring device is connected to the control unit 26. Alternatively, a wireless data link may be installed between the respiration monitoring device and the control unit 26 by employing suitable wireless data transfer means. The control unit 26 of the magnetic resonance imaging system 10 is configured for receiving the output signal 48 from the respiration monitoring device for triggering guidance, as will be described in more detail later on.

Figure 4:
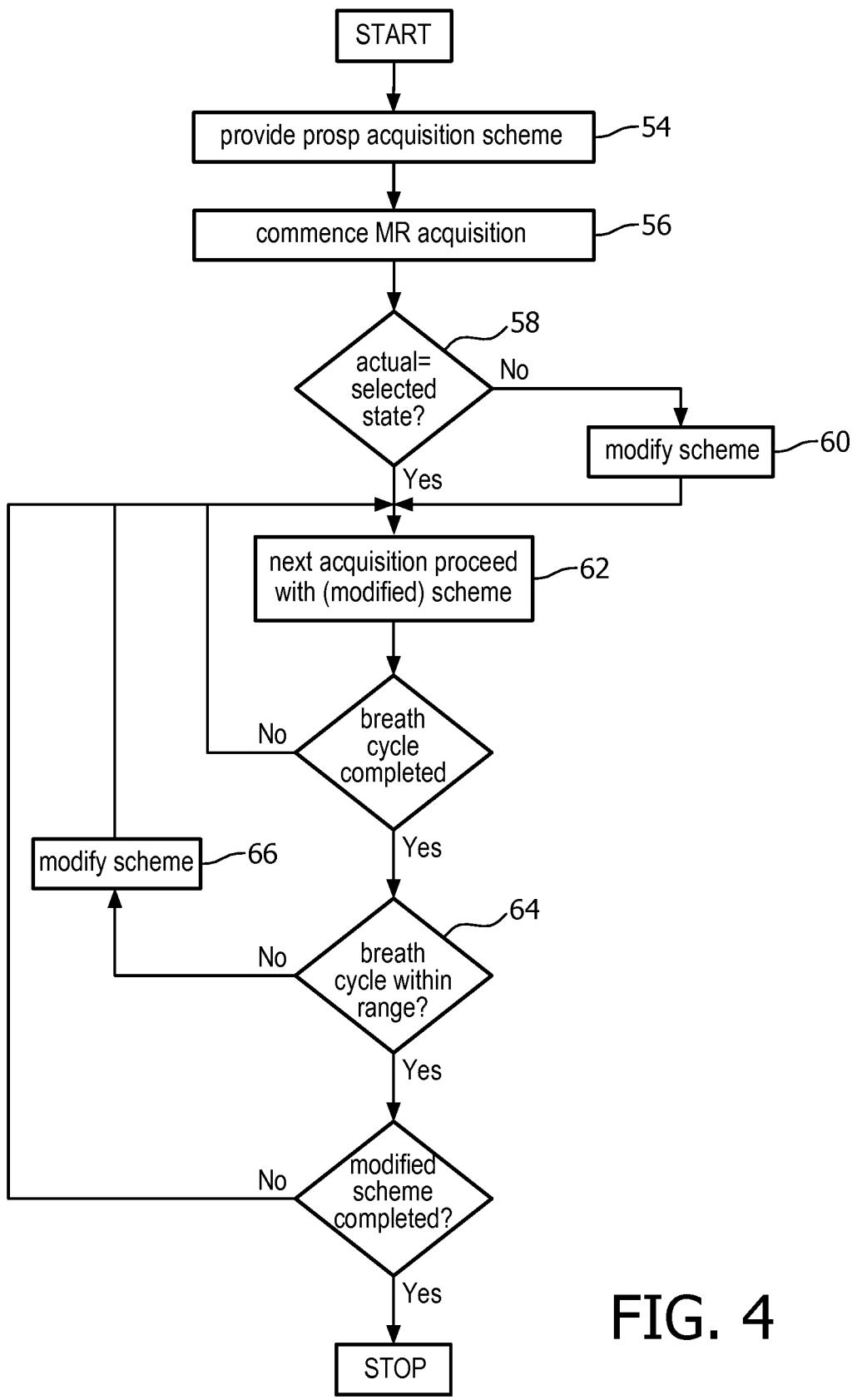
FIG. 4 shows a flow chart of an embodiment of the method in accordance with the invention.

In the following, an embodiment of a method of operating the magnetic resonance imaging system 10 with regard to triggering of magnetic resonance image acquisitions is described. A principal flow chart of the method is given in FIG. 4. In preparation of operating the magnetic resonance imaging system 10, it shall be understood that all involved units and devices are in an operational state and configured as illustrated in FIG. 1.

In order to be able to carry out the method as a specific operation of the magnetic resonance imaging system 10, the control unit 26 comprises a software module 44 (FIG. 1). The method steps to be conducted are converted into a program code of the software module 44, wherein the program code is implementable in a memory unit 30 of the control unit 26 and is executable by a processor unit 32 of the control unit 26.

In a first step 54 of the method, a prospective acquisition scheme for acquiring within the plurality of breathing cycles 50 one magnetic resonance image of each slice of the set of selected slices at each respiration state of the set of selected respiration states of the subject of interest 20 is provided. The set of selected respiration states consists of the eight respiration states of 0% inspiration, 25% inspiration, 50% inspiration, 75% inspiration, 100% inspiration, 75% expiration, 50% expiration and 25% expiration, and the set of selected slices comprises 32 slices. The prospective acquisition scheme of this embodiment is interleaved but may in general also be non-interleaved. The provided interleaved prospective acquisition scheme may be similar to the prior art acquisition scheme described in the paper by Y. Hu et al. mentioned in chapter "Background of the Invention" of this application. The triggering for acquiring a magnetic resonance image at one of the selected respiration states is based on predetermined threshold output signal levels of the respiration monitoring device. The predetermined threshold output signal levels are stored in the memory unit 30 of the control unit 26.

Figure 3:
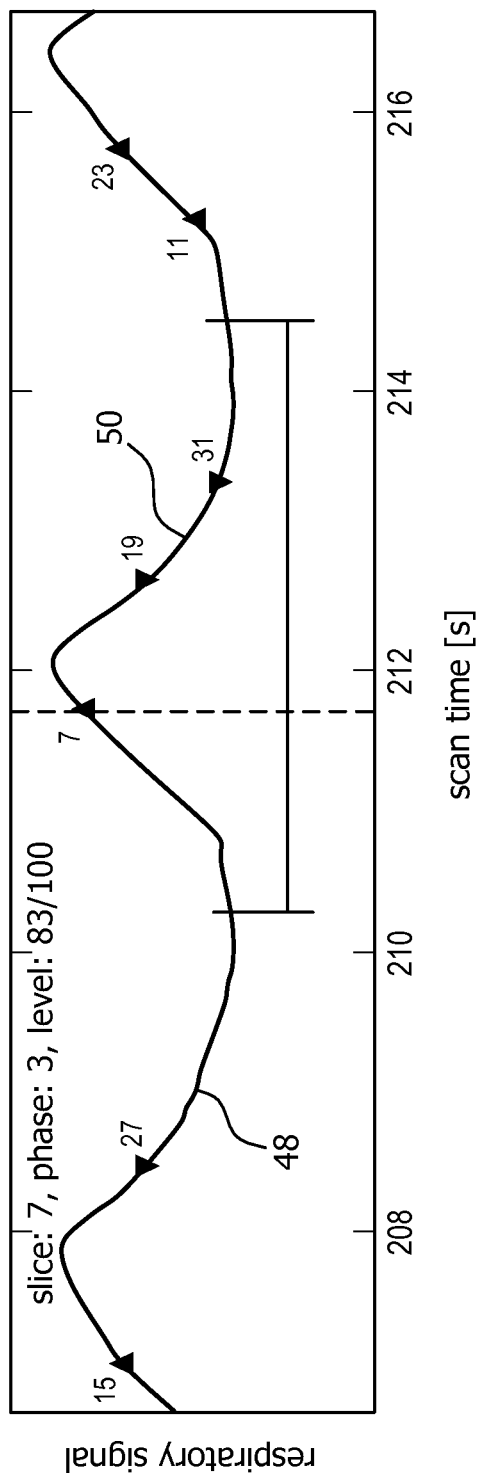
FIG. 3 is a detailed partial view of the graph pursuant to FIG. 2.

In a next step 56 of the method, the magnetic resonance image acquisition pursuant to the provided prospective acquisition scheme commences. In the detailed view of the output signal of the respiration monitoring device of FIG. 3 triggering at the predetermined threshold output signal levels is indicated by triangles, with triangles pointing up denoting inspiration and triangles pointing down meaning expiration. During executing the magnetic resonance image acquisition pursuant to the prospective acquisition scheme, actual respiration states at which magnetic resonance images were actually acquired, are compared with the selected respiration states according to the prospective acquisition scheme and predetermined ranges of tolerance 52 of the selected respiration states in a next step 58. The predetermined ranges of tolerance 52 of the selected respiration states are a fixed percentage of, for instance, ±5% of the predetermined threshold output signal levels.

If it is determined that one of the actual respiration states lies outside the predetermined range of tolerance 52 of the selected respiration state, the prospective acquisition scheme is modified in another step 60. As an example, in the time period at about 212 s, highlighted in FIG. 2 and shown in detail in FIG. 3, the magnetic resonance image to be acquired at the selected respiration state of 100% inspiration was actually acquired at an output signal level of 83% because the respiratory output signal amplitude in this breathing cycle 50 was high above average.

The step 60 of modifying the prospective acquisition scheme comprises discarding the acquired data representing the magnetic resonance image corresponding to the actual respiration state of 83% that lies outside the predetermined range of tolerance 52 of the selected respiration state, and adding the selected respiration state that corresponds to the actual respiration state of 83% lying outside the predetermined range of tolerance 52 of the selected respiration state to the prospective acquisition scheme as a selected respiration state at which another magnetic resonance image is still to be acquired.

After the step 60 of modifying the prospective acquisition scheme, the execution of magnetic resonance imaging acquisition pursuant to the modified prospective acquisition scheme is proceeded with as a next step 62.

If for a specific breathing cycle 50 all the magnetic resonance images scheduled in the prospective acquisition scheme have been acquired, a step 64 of comparing the output signal time course representing the breathing cycle 50 is carried out. The comparison is performed with a predetermined standard output signal time course 68 representing a standard breathing cycle and having predetermined standard output signal ranges of tolerance 52. The predetermined standard output signal time course 68 has been obtained by averaging output signal time courses over a plurality of breathing cycles of the subject of interest 20 in a preparatory phase prior to commencing the acquisition of magnetic resonance images. The predetermined standard output signal ranges of tolerance 52 are a fixed percentage of, in this embodiment, ±5% of the predetermined standard output signal time course 68 (FIG. 2; the predetermined standard output signal ranges of tolerance 52 are overstated for clarity purposes).

If in the course of the step 64 of comparing it is determined that the output signal time course representing the breathing cycle 50 for which all the magnetic resonance images scheduled in the prospective acquisition scheme have been acquired, at least partially lies outside the predetermined ranges of tolerance 52 of the predetermined standard output signal time course 68, another step 66 of modifying the prospective acquisition scheme is carried out.

Figure 2:
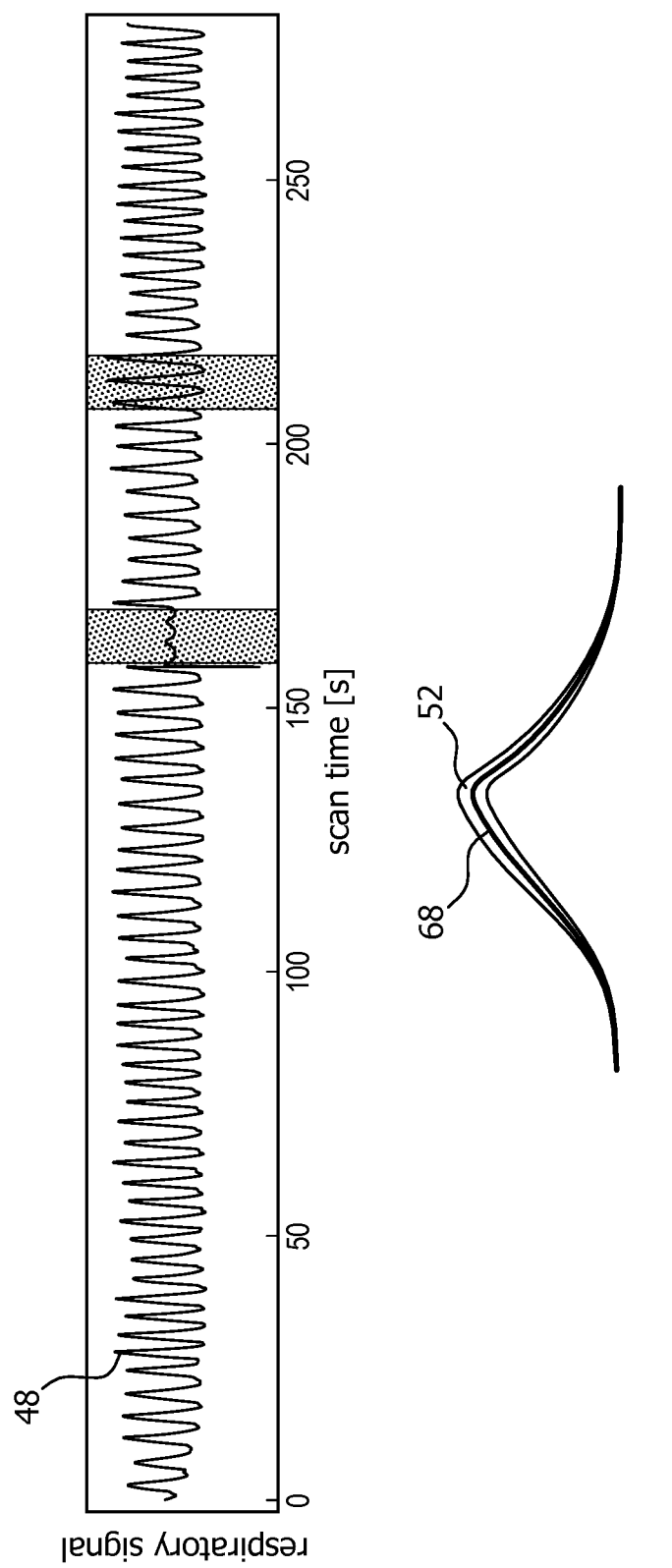
FIG. 2 is a graph of an output signal of a respiration monitoring means.

As an example, in the time period at about 160 s which is highlighted in FIG. 2, the respiration sensor failed for about 15 s. Nonetheless, magnetic resonance images have been acquired at various selected respiration states. Obviously, in this time period the output signal representing a breathing cycle partially lies outside the predetermined ranges of tolerance 52 of the predetermined standard output signal time course 68.

The step 66 of modifying the prospective acquisition scheme comprises discarding acquired the data representing magnetic resonance images corresponding to all selected respiration states of the breathing cycle 50 that at least partially lies outside the predetermined ranges of tolerance 52 of the predetermined standard output signal time course 68. Also, in the step 66 of modifying, the selected respiration states that correspond to the breathing cycle 50 that at least partially lies outside the predetermined ranges of tolerance 52 of the predetermined standard output signal time course 68 are added to the prospective acquisition scheme as selected respiration states at which magnetic resonance images are still to be acquired.

If the modified prospective acquisition scheme is finalized, the magnetic resonance images are acquired at the intended and selected respiration states, which provides an improved image quality of the acquired 4D magnetic resonance image data set due to a smaller systematic error regarding an assignment of the acquired magnetic resonance image to the respiration state of the subject of interest 20.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

REFERENCE SYMBOL LIST 10 magnetic resonance imaging system
12 scanner unit
14 main magnet
16 examination space
18 center axis
20 subject of interest
22 magnetic gradient coil system
24 radio frequency transmitter unit
26 control unit
28 human interface device
30 memory unit
32 processor unit
34 radio frequency antenna device (transmit)
36 radio frequency antenna device (receive)
38 radio frequency switching unit
40 radio frequency shield
42 signal processing unit
44 software module
46 respiration monitoring means
48 output signal
50 breathing cycle
52 range of tolerance
54 step of providing prospective acquisition scheme
56 step of commencing magnetic resonance image acquisition
58 step of comparing actual to selected respiration states
60 step of modifying the prospective acquisition scheme
62 step of proceeding with modified prospective acquisition scheme
64 step of comparing
66 step of modifying the prospective acquisition scheme
68 standard output signal time course
$B_0$ static magnetic field
$B_1$ radio frequency excitation field

The invention claimed is:

1. A method of operating a magnetic resonance imaging system, the magnetic resonance imaging system being configured for acquiring magnetic resonance images of a set of slices from at least a portion of a subject of interest over at least one breathing cycle of the subject of interest, and the magnetic resonance imaging system being connectable to a respiration monitor which is configured to provide an output signal whose level represents a respiration state of the subject of interest, the method comprising:
  a step of providing a prospective acquisition scheme for acquiring within the at least one breathing cycle at least one magnetic resonance image of each slice of the set of slices at each respiration state of a set of selected respiration states of the subject of interest, the prospective acquisition scheme being configured to provide the selected respiration states to trigger magnetic resonance image acquisition based on predetermined threshold output signal levels of the respiration monitor,
  a step of acquiring magnetic resonance images pursuant to the provided prospective acquisition scheme,
  during magnetic resonance image acquisition pursuant to the prospective acquisition scheme, a step of comparing actual respiration states at which magnetic resonance images were actually acquired, with the selected respiration states according to the prospective acquisition scheme and predetermined ranges of tolerance of the selected respiration states,
  a step of modifying the prospective acquisition scheme to provide a modified prospective acquisition scheme, if one of the actual respiration states lies outside the predetermined range of tolerance of the selected respiration state, and
  a step of executing magnetic resonance imaging acquisition pursuant to the modified prospective acquisition scheme,
  a step of comparing a time course of an output signal representing a breathing cycle for which all the magnetic resonance images scheduled in the prospective acquisition scheme have been acquired, with a predetermined standard output signal time course representing a standard breathing cycle and having predetermined standard output signal ranges of tolerance, and
  a step of further modifying the prospective acquisition scheme to provide a further modified prospective acquisition scheme if the time course of the output signal representing the breathing cycle for which all the magnetic resonance images scheduled in the prospective acquisition scheme have been acquired at least partially lies outside the predetermined ranges of tolerance of the predetermined standard output signal time course, and
  a step of executing magnetic resonance imaging acquisition pursuant to the further modified prospective acquisition scheme.

2. The method as claimed in claim 1, wherein the predetermined ranges of tolerance of the selected respiration states—are a fixed percentage of the predetermined threshold output signal levels.

3. The method as claimed in claim 1, wherein the step of modifying the prospective acquisition scheme comprises:
  discarding acquired data representing a magnetic resonance image corresponding to an actual respiration state that lies outside the predetermined range of tolerance of the selected respiration state, and
  adding the selected respiration state that corresponds to the actual respiration state lying outside the predetermined range of tolerance of the selected respiration state to the prospective acquisition scheme as a selected respiration state at which another magnetic resonance image is still to be acquired to generate the modified prospective acquisition scheme.

4. The method as claimed in claim 1, wherein the step of further modifying the prospective acquisition scheme comprises:
  discarding acquired data representing magnetic resonance images corresponding to all selected respiration states of a breathing cycle that at least partially lies outside the predetermined ranges of tolerance of the predetermined standard output signal time course, and
  adding the selected respiration states that correspond to the breathing cycle that at least partially lies outside the predetermined ranges of tolerance of the predetermined standard output signal time course to the prospective acquisition scheme as selected respiration states at which magnetic resonance images are still to be acquired to generate the further modified prospective acquisition scheme.

5. The method as claimed in claim 1, wherein the predetermined standard output signal ranges of tolerance are a fixed percentage of the predetermined standard output signal time course.

6. A magnetic resonance imaging system configured for acquiring magnetic resonance images of a set of slices from at least a portion of a subject of interest over at least one breathing cycle of the subject of interest, comprising:
  an examination space provided to position the subject of interest within;
  a main magnet configured for generating a static magnetic field $B_0$ in the examination space;

a magnetic gradient coil system configured for generating gradient magnetic fields superimposed to the static magnetic field $B_0$;

at least one radio frequency antenna device that is configured for applying a radio frequency excitation field $B_1$ to nuclei of or within the portion of the subject of interest for magnetic resonance excitation;

at least one radio frequency antenna device that is provided for receiving magnetic resonance signals from the nuclei of or within the portion of the subject of interest that have been excited by applying the radio frequency excitation field $B_1$;

a control unit for controlling at least one function of the magnetic resonance imaging system;

a signal processing unit configured for processing magnetic resonance signals to determine images of slices of at least the portion of the subject of interest from the received magnetic resonance signals;

wherein the control unit is configured for receiving an output signal from a respiration monitor for triggering guidance, wherein a level of the output signal represents a respiration state of the subject of interest, and wherein the control unit is configured to carry out steps of:

providing a prospective acquisition scheme for acquiring within the at least one breathing cycle at least one magnetic resonance image of each slice of the set of slices at each respiration state of a set of selected respiration states of the subject of interest, the prospective acquisition scheme being configured to provide the selected respiration states to trigger magnetic resonance image acquisition based on predetermined threshold output signal levels of the respiration monitor, acquiring magnetic resonance images pursuant to the provided prospective acquisition scheme, during magnetic resonance image acquisition pursuant to the prospective acquisition scheme, comparing actual respiration states at which magnetic resonance images were actually acquired, with the selected respiration states according to the prospective acquisition scheme and predetermined ranges of tolerance of the selected respiration states, modifying the prospective acquisition scheme to provide a modified prospective acquisition scheme, if one of the actual respiration states lies outside the predetermined range of tolerance of the selected respiration state, comparing a time course of an output signal representing a breathing cycle for which all the magnetic resonance images scheduled in the prospective acquisition scheme have been acquired, with a predetermined standard output signal time course representing a standard breathing cycle and having predetermined standard output signal ranges of tolerance, further modifying the prospective acquisition scheme to provide a further modified prospective acquisition scheme if the time course of the output signal representing the breathing cycle for which all the magnetic resonance images scheduled in the prospective acquisition scheme have been acquired at least partially lies outside the predetermined ranges of tolerance of the predetermined standard output signal time course, and executing magnetic resonance imaging acquisition pursuant to the further modified prospective acquisition scheme.

7. The magnetic resonance imaging system as claimed in claim 6, wherein the at least one radio frequency antenna device that is configured for applying a radio frequency excitation field $B_1$ is provided with radio frequency pulse sequences that are suitable for obtaining T2-weighted magnetic resonance images.

8. The magnetic resonance imaging system as claimed in claim 6, wherein the control unit is further configured to modify the prospective acquisition scheme by:

discarding acquired data representing a magnetic resonance image corresponding to an actual respiration state that lies outside the predetermined range of tolerance of the selected respiration state, and adding the selected respiration state that corresponds to the actual respiration state lying outside the predetermined range of tolerance of the selected respiration state to the prospective acquisition scheme as a selected respiration state at which another magnetic resonance image is still to be acquired.

9. The magnetic resonance imaging system as claimed in claim 6, wherein the control unit is further configured to modify the prospective acquisition scheme by:

discarding acquired data representing magnetic resonance images corresponding to all selected respiration states of a breathing cycle that at least partially lies outside the predetermined ranges of tolerance of the predetermined standard output signal time course, and adding the selected respiration states that correspond to the breathing cycle that at least partially lies outside the predetermined ranges of tolerance of the predetermined standard output signal time course to the prospective acquisition scheme as selected respiration states at which magnetic resonance images are still to be acquired.

10. A non-transitory computer readable memory having encoded thereon, a software module executable by a computer processor to perform the steps of:

providing a prospective acquisition scheme for acquiring within the at least one breathing cycle at least one magnetic resonance image of each slice of the set of slices at each respiration state of a set of selected respiration states of the subject of interest, the prospective acquisition scheme providing the selected respiration states for triggering magnetic resonance image acquisition based on predetermined threshold output signal levels of a respiration monitor, receiving magnetic resonance images acquired pursuant to the provided prospective acquisition scheme, comparing actual respiration states at which magnetic resonance images were actually acquired with the selected respiration states according to the prospective acquisition scheme and predetermined ranges of tolerance of the selected respiration states, modifying the prospective acquisition scheme to provide a modified prospective acquisition scheme, if one of the actual respiration states lies outside the predetermined range of tolerance of the selected respiration state, and comparing a time course of an output signal representing a breathing cycle for which all the magnetic resonance images scheduled in the prospective acquisition scheme have been acquired, with a predetermined standard output signal time course representing a standard breathing cycle and having predetermined standard output signal ranges of tolerance, further modifying the prospective acquisition scheme to provide a further modified prospective acquisition scheme if the time course of the output signal representing the breathing cycle for which all the magnetic resonance images scheduled in the prospective acquisition scheme have been acquired at least partially lies outside the predetermined ranges of tolerance of the predetermined standard output signal time course.

11. The non-transitory computer readable memory of claim 10, wherein the software module is further executable by the computer processor to further perform the steps of:
discarding acquired data representing magnetic resonance images corresponding to all selected respiration states of a breathing cycle that at least partially lies outside the predetermined ranges of tolerance of the predetermined standard output signal time course, and
adding the selected respiration states that correspond to the breathing cycle that at least partially lies outside the predetermined ranges of tolerance of the predetermined standard output signal time course to the prospective acquisition scheme as selected respiration states at which magnetic resonance images are still to be acquired to generate the further modified prospective acquisition scheme.

\* \* \* \* \*